United States Patent
Wang (10) Patent No.: US 10,722,398 B2
(45) Date of Patent: Jul. 28, 2020

(54) EYE DOCKING FOR LASER EYE SURGERY

(71) Applicant: AMO Development, LLC, Santa Ana, CA (US)

(72) Inventor: Bing Wang, Pleasanton, CA (US)

(73) Assignee: AMO Development, LLC, Santa Ana, CA (US)

(*) Notice: Subject to any disclaimer, the term of this patent is extended or adjusted under 35 U.S.C. 154(b) by 383 days.

(21) Appl. No.: 15/480,260

(22) Filed: Apr. 5, 2017

(65) Prior Publication Data

US 2017/0281404 A1    Oct. 5, 2017

Related U.S. Application Data

(60) Provisional application No. 62/318,673, filed on Apr. 5, 2016.

(51) Int. Cl.
*A61F 9/008* (2006.01)
*A61F 9/009* (2006.01)

(52) U.S. Cl.
CPC .............. *A61F 9/008* (2013.01); *A61F 9/009* (2013.01)

(58) Field of Classification Search
CPC .................................. A61F 9/008; A61F 9/009
See application file for complete search history.

(56) References Cited

U.S. PATENT DOCUMENTS

| | | | |
|---|---|---|---|
| 5,336,215 A * | 8/1994 | Hsueh | A61F 9/008 606/10 |
| 7,390,089 B2 | 6/2008 | Loesel et al. | |
| 7,955,324 B2 | 6/2011 | Melcher et al. | |
| 8,398,238 B1 * | 3/2013 | Juhasz | A61F 9/008 351/208 |

(Continued)

FOREIGN PATENT DOCUMENTS

| | | |
|---|---|---|
| CA | 2857342 A1 | 6/2013 |
| EP | 2913036 A1 | 9/2015 |

(Continued)

OTHER PUBLICATIONS

H2W, "Voice Coil Actuators", https://web.archive.org/web/20160315042249/https://www.h2wtech.com/category/voice-coil-actuators#productInfo1, page captured on Mar. 15, 2016 by the internet archive, viewed on Apr. 11, 2019.*

(Continued)

*Primary Examiner* — Christopher Koharski
*Assistant Examiner* — James Moss
(74) *Attorney, Agent, or Firm* — Johnson & Johnson Surgical Vision, Inc.

(57) ABSTRACT

A laser surgery system includes: a gantry configured to be attached to a structural frame; a docking receptacle configured to be removably attached to an eye docking assembly which is attached to an eye; an adjustable table attached to the gantry; a lens assembly attached to the adjustable table, wherein the adjustable table is configured to move the lens assembly relative to the eye; one or more connectors configured to attach the docking receptacle to the gantry, at least one of the connectors being configured to dynamically adjust the distance between a surface of the gantry and a surface of the docking receptacle; and a controller configured to maintain a target distance between the lens assembly and a reference area of the eye docking assembly.

9 Claims, 4 Drawing Sheets (56) References Cited

U.S. PATENT DOCUMENTS

| | | | |
|---|---|---|---|
| 8,512,236 B2 | 8/2013 | Gertner et al. | |
| 9,044,304 B2* | 6/2015 | Raksi | A61F 9/009 |
| 2004/0254568 A1* | 12/2004 | Rathjen | A61F 9/00827 |
| | | | 606/4 |
| 2010/0228236 A1* | 9/2010 | Muhlhoff | A61F 9/0027 |
| | | | 606/4 |
| 2012/0078241 A1 | 3/2012 | Gooding et al. | |
| 2013/0072917 A1* | 3/2013 | Kaschke | A61F 9/00736 |
| | | | 606/6 |
| 2013/0338649 A1* | 12/2013 | Hanebuchi | A61F 9/009 |
| | | | 606/4 |
| 2013/0345682 A1 | 12/2013 | Hailmann et al. | |
| 2014/0107634 A1 | 4/2014 | Vogler et al. | |
| 2014/0114294 A1* | 4/2014 | Heitel | A61F 9/00802 |
| | | | 606/4 |
| 2014/0128821 A1 | 5/2014 | Gooding et al. | |
| 2014/0128852 A1 | 5/2014 | Gooding et al. | |
| 2014/0216468 A1 | 8/2014 | Goldshleger et al. | |
| 2015/0335479 A1* | 11/2015 | Shibata | A61F 9/00825 |
| | | | 606/5 |
| 2016/0310317 A1* | 10/2016 | Gooding | A61F 9/009 |
| 2017/0120377 A1* | 5/2017 | Webster | A61B 18/20 |

FOREIGN PATENT DOCUMENTS

| | | | |
|---|---|---|---|
| JP | 2013248303 A | 12/2013 | |
| WO | 2008150331 A1 | 12/2008 | |

OTHER PUBLICATIONS

International Search Report and Written Opinion for Application No. PCT/US2017/026229, dated Aug. 14, 2017, 14 pages.

\* cited by examiner

EYE DOCKING FOR LASER EYE SURGERY

RELATED APPLICATIONS

This application claims priority to, and the benefit of, under 35 U.S.C. § 119(e) of U.S. Provisional Appl. No. 62/318,673, filed Apr. 5, 2016, which is incorporated by reference herein in its entirety.

TECHNICAL FIELD

Embodiments of this invention pertain to laser eye surgery, and in particular to arrangements for docking an eye to a laser surgery instrument during laser eye surgery.

BACKGROUND

With significant developments in laser technology and its application to ophthalmology, laser surgery has become the technique of choice for ophthalmic procedures, such as refractive surgery for correcting myopia, hyperopia, astigmatism, and so on, and cataract surgery for treating and/or removing a cataractic lens. Often, a surgeon may prefer a surgical laser beam over manual surgical tools like microkeratomes because the laser beam can be focused precisely on extremely small amounts of eye tissue, thereby enhancing accuracy and reliability of the procedure.

Laser eye surgery generally uses different types of laser beams, such as ultraviolet lasers, infrared lasers, and near infrared, ultra-short pulsed lasers for various procedures and indications. For example, in the commonly-known LASIK (Laser Assisted In Situ Keratomileusis) procedure, an ultra-short pulsed laser is used to cut a corneal flap to expose the corneal stroma for photoablation with an excimer laser that operates in the ultraviolet range. Non-ultraviolet, ultra-short pulsed lasers emit radiation with pulse durations as short as 10 femtoseconds and as long as 3 nanoseconds, and a wavelength between 300 nm and 3000 nm. Besides cutting corneal flaps, ultra-short pulsed laser systems can also be used to perform cataract-related surgical procedures, including opening cataract incisions, capsulotomy, as well as softening and/or breaking of the cataractous lens. They can further be used for lenticule extraction procedures for refractive correction. Examples of laser systems that provide ultra-short pulsed laser beams include Abbott Medical Optics Inc.'s iFS Advanced Femtosecond Laser System and CATALYS Precision Laser System.

Optics and lenses for laser systems are typically complex and expensive. Instead of using an expensive lens with a large radius, some laser systems use a beam delivery system to move a lens assembly near an eye to direct the laser beam to different areas of the eye for surgery with a desired small spot size, thereby reducing system cost. The mechanical system which moves the lens assembly must do so with very precise motion control (e.g., micron level accuracy) and at a relatively high rate of speed, and is typically quite heavy.

In addition, it is necessary to stabilize patient's eye during laser surgery in a predetermined position relative to the focal point of the laser beam. This is normally done by physically constraining eye movement during laser surgery by applying an eye docking assembly to the patient's eye prior to the surgery. The eye docking assembly is fixed to the laser surgery system on the one end, and fixes an applanating lens in a patient interface onto the patient's eye on the other end.

During eye surgery under such circumstances, system vibrations have to be maintained so that they are very low, or else any unbalanced vibrations will be applied to the eye.

As noted above, however, in a system where a beam delivery system moves a lens assembly during the surgery, it is very difficult to eliminate vibrations. Furthermore, in the case of a loss of electrical power, it is possible that the weight of the beam delivery system may be transferred to the patient's eye.

Accordingly, it would be desirable to provide an arrangement and method whereby the eye of a patient during laser surgery may be maintained in a predetermined position relative to the focal point of a laser beam during laser surgery while reducing the loading imposed upon the eye by any vibrations or movement of the laser eye surgery equipment.

SUMMARY OF INVENTION

Hence, to obviate one or more problems due to limitations or disadvantages of the related art, in one aspect, this disclosure provides embodiments for a system comprising: a structural frame; a gantry attached to the structural frame and movable relative to the structural frame; a docking receptacle configured to be removably attached to an eye docking assembly which is attached to an eye; one or more connectors configured to resiliently attach the docking receptacle to the gantry; an adjustable table attached to the gantry and movable in three mutually orthogonal directions relative to the gantry; a lens assembly attached to the adjustable table, wherein the adjustable table is configured to move the lens assembly in the three mutually orthogonal directions relative to the eye; at least one sensor configured to sense at least one of (1) a distance between a surface of the gantry and a surface of the docking receptacle which is attached resiliently to the gantry by the one or more connectors, and (2) a change in the distance between the surface of the gantry and the surface of the docking receptacle, and in response thereto to output at least one sensing signal; and a controller configured to control movement of the adjustable table in response to the at least one sensing signal to maintain a target distance between the lens assembly and a reference area of the eye docking assembly.

In some embodiments, the system further includes the laser source, wherein the laser source is fixed to the structural frame.

In some embodiments, the one or more connectors include one or more springs which resiliently connect the docking receptacle to the gantry.

In some versions of these embodiments, the one or more connectors include one or more voice coils.

In some versions of these embodiments, the controller is configured to control an amount of current which passes through at least one voice coil to control a docking force between the docking receptacle and the eye docking assembly.

In some versions of these embodiments, the controller is configured to control the amount of current which passes through at least one voice coil in response to the at least one sensing signal.

In some embodiments, the one or more connectors comprise one or more voice coils.

In some versions of these embodiments, the controller is configured to control an amount of current which passes through at least one voice coil to control a docking force between the docking receptacle and the eye docking assembly.

In some versions of these embodiments, the controller is configured to control the amount of current which passes through at least one voice coil in response to the at least one sensing signal.

In some embodiments, the adjustable table includes: a first arrangement configured to move the lens assembly in response to the controller in an X direction and a Y direction which is orthogonal to the X direction; and a Z stage configured to move the lens assembly in response to the controller in a Z direction which is orthogonal to the X direction and the Y direction so as to focus the laser light at a desired depth of the eye.

In some versions of these embodiments, the system further comprises a Z stage sensor configured to sense a displacement of the Z stage with respect to the gantry and in response thereto to output a Z stage position sensing signal, wherein the controller is configured to control movement of Z stage in response to the Z stage position sensing signal to maintain the target distance between the lens assembly and the reference area of the eye docking assembly.

In some embodiments, the system further comprises an imaging device configured to produce image data for the eye, wherein the controller is configured to use the image data to control the gantry to dock the eye docking assembly to the docking receptacle.

In another aspect, the method comprises: sensing at least one of (1) a distance between a surface of a gantry and a surface of a docking receptacle which is attached resiliently to the gantry by one or more connectors, and (2) a change in the distance between the surface of the gantry and the surface of the docking receptacle, and in response thereto outputting at least one sensing signal, wherein the docking receptacle is removably attached to an eye docking assembly which is attached to an eye; passing a laser beam from a laser source through a lens assembly which is attached to an adjustable table which is attached to the gantry and which adjustable table is configured to move the lens assembly in three dimensions with respect to the eye; the adjustable table moving the lens assembly in three dimensions relative to the eye so as to direct the laser beam to one or more target areas of the eye to perform a laser surgery on the eye; and controlling movement of the adjustable table in response to the at least one sensing signal to maintain focus of the laser beam at a desired depth of the eye.

In some embodiments, the adjustable table includes: a first arrangement configured to move the lens assembly in an X direction and a Y direction which is orthogonal to the X direction, and a Z stage configured to move the lens assembly in a Z direction which is orthogonal to the X direction and the Y direction, and controlling movement of the adjustable table in response to the at least one sensing signal includes controlling movement of the Z stage to maintain a desired distance between the lens assembly and a reference area of the eye docking assembly.

In some embodiments, the one or more connectors comprise one or more voice coils, the method further comprising controlling an amount of current which passes through at least one voice coil to adjust a distance between the surface of the gantry and the surface of the docking receptacle.

In another aspect, the system comprises: a gantry configured to be attached to a structural frame; a docking receptacle configured to be removably attached to an eye docking assembly which is attached to an eye; an adjustable table movable in three dimensions and attached to the gantry; a lens assembly attached to the adjustable table, wherein the adjustable table is configured to move the lens assembly relative to the eye; one or more connectors configured to attach the docking receptacle to the gantry, at least one of the connectors being configured to dynamically adjust a distance between a surface of the gantry and a surface of the docking receptacle; and a controller configured to maintain a target distance between the lens assembly and a reference area of the eye docking assembly.

In some embodiments, the one or more connectors comprise at least one spring which resiliently connects the docking receptacle to the gantry.

In some embodiments, the one or more connectors comprise one or more voice coils, wherein the controller is configured to maintain the target distance between the lens assembly and a reference area of the eye docking assembly by at least one of (1) controlling movement of the adjustable table in a direction from the lens assembly to the eye docking assembly, and (2) controlling an amount of current passing through the one or more voice coils.

In some embodiments, the system further comprises at least one sensor configured to sense at least one of (1) a distance between the surface of the gantry and the surface of the docking receptacle, and (2) a change in the distance between the surface of the gantry and the surface of the docking receptacle, and in response thereto outputting at least one sensing signal.

In some versions of these embodiments, the controller is configured to maintain the target distance between the lens assembly and a reference area of the eye docking assembly in response to the at least one sensing signal by controlling a movement of the adjustable table in a direction from the lens assembly to the eye docking assembly.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of laser surgery systems and eye stabilization devices are described below to illustrate various aspects and advantages of these devices and methods are described below. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description. It should be understood that the principles involved in these devices and methods can be employed in a variety of other contexts, and therefore the novel devices and method disclosed and claimed here should not be construed as being limited to the example embodiments described below.

Figure 1:
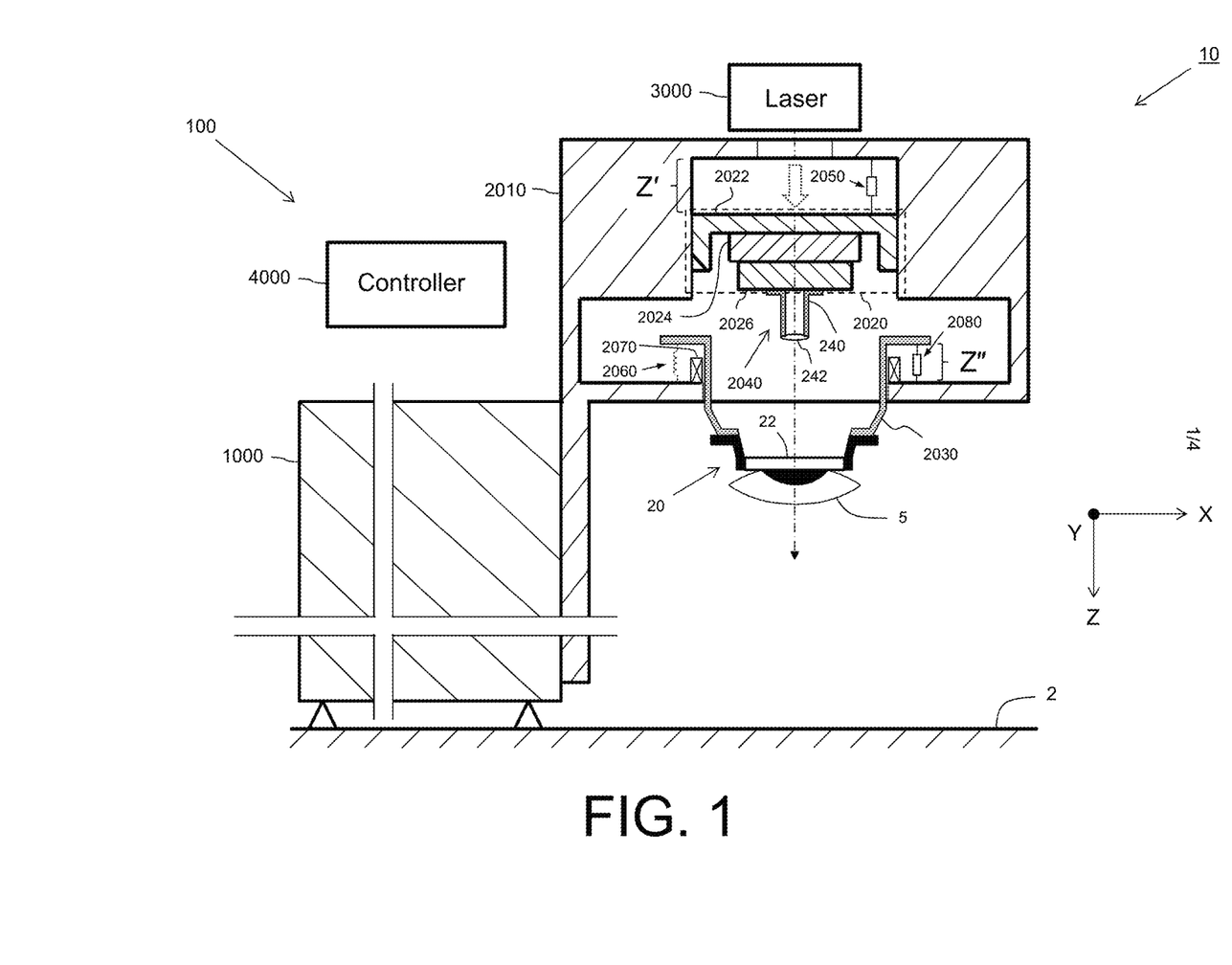
FIG. 1 illustrates an example embodiment of an arrangement of a laser surgery system and an eye stabilization device.

FIG. 1 illustrates an example embodiment of an arrangement 10 of a laser surgery system 100 and an eye stabilization device. FIG. 1 also illustrates a coordinate system for arrangement 10, including an X direction (horizontal in FIG. 1), a Y direction (in and out of the page in FIG. 1), and a Z direction (vertical in FIG. 1).

Laser surgery system 100 includes a structural frame or base 1000, a gantry 2010 movable in three dimensions and attached to the structural frame; an adjustable table 2020 attached to gantry 2010; a docking receptacle 2030; a lens assembly 2040 attached to adjustable table 2020; one or more sensors 2050; one or more connectors 2060 and 2070 which resiliently connect docking receptacle 2030 to gantry 2010; one or more sensors 2080; a laser 3000; and a controller 4000.

Here, the eye stabilization device comprises an eye docking assembly 20 including an applanating lens 22. Eye docking assembly 20 is configured to be docked or connected to docking receptacle 2030 to form a patient interface for laser surgery. Beneficially, eye docking assembly 20 is a single-use disposable element which is attached to an eye 5 of a patient in advance of laser surgery.

FIG. 1 is a sort of "hybrid" illustration which illustrates certain structural elements such as structural frame 1000, gantry 2010, adjustable table 2020, docking receptacle 2030, lens assembly 2040, and eye docking assembly cross-sectionally, and which shows other elements such as sensor(s) 2050, connector(s) 2070, sensor 2080, laser 3000, and controller 4000 as functional blocks.

Lens assembly 2040 includes a lens 242 and an optical structure 240 holding lens 242 and providing an optical path for laser light from laser 3000 to pass through lens assembly 2040, and specifically to pass through lens 242.

In some embodiments, one or more of connector(s) 2060 may be a spring. In some embodiments, one or more of connector(s) 2070 may be a voice coil.

In some embodiments, structural frame 1000 may be fixed or attached to ground 2, for example by one or more bolts. In other embodiments, structural frame 1000 may not be fixed to ground 2, and may include one or more wheels which allow it to be moved. Beneficially, the wheels may have a locking mechanism so that laser surgery system 100 does not move once it is placed in position for a laser surgery. Beneficially, structural frame 1000 may have a substantial mass and weight, for example several tens of pounds or more (e.g., 200 pounds), so as to create a substantial frictional force between structural frame 1000 and ground 2.

Controller 4000 may include one or more processors and associated memory (e.g., random access memory (RAM), FLASH memory, read only memory (ROM), etc.) which may store therein computer-readable instructions for one or more algorithms to be executed by the processor(s) of controller 4000. Although not shown in FIG. 1, controller 4000 may receive one or more sensing signals from sensor(s) 2050 and/or sensor(s) 2080, and may provide one or more control signals to adjustable table 2020, connector (e.g., voice coil) 2070, and/or laser 3000 to control operations thereof.

Gantry 2010 is attached the structural frame 1000 and is movable relative to structural frame 1000, and in particular movable in the Z direction.

Adjustable table 2020 is attached to gantry 2010. Beneficially, adjustable table 2020 is movable in three mutually orthogonal directions (e.g., the X direction, the Y direction, and the Z direction) relative to gantry 2010. Adjustable table 2020 is configured to move lens assembly 2040 in the three mutually orthogonal directions relative to eye 5. Beneficially, adjustable table 2020 may be moved under control of one or more control signals received from controller 4000.

Here, adjustable table 2020 includes a first arrangement of an X stage 2026 and a Y stage 2024 configured to move lens assembly 2040 in the X direction and Y direction, and a Z stage 2022 configured to move the lens assembly in the Z direction in response to one or more control signals from controller 4000 so as to focus the laser light at a desired depth of the patient's eye 5 for laser surgery.

Beneficially, one or more sensor(s) 2050 sense the distance Z' between a surface of gantry 2010 and a surface of adjustable table 2020, and in response thereto output(s) to controller 4000 one or more sensing signals. In some embodiments, one or more sensor(s) 2050 may sense a change in the distance Z' between the surface of gantry 2010 and the surface of adjustable table 2020, and in response thereto output(s) to controller 4000 one or more sensing signals.

Connector(s) 2060 and 2070 resiliently attach docking receptacle 2030 to gantry 2010. Here, "resiliently" is understood to mean connected in such a way that the docking receptacle 2030 and gantry 2010 may move relative to each other in response to external forces. In particular, for example, connector(s) 2060 may comprise springs which may compress and expand in response to external forces, and connector(s) 2060 may comprise voice coils which may move by the reaction of a magnetic field in response to a current passing through it, for example a current supplied by controller 4000. Connectors 2060 and 2070 connect docking receptacle 2030 and gantry 2010 so that there is a distance Z" between a surface of gantry 2010 and a surface of docking receptacle 2030 which is attached resiliently to gantry 2010. Connector(s) 2060 and 2070 may dynamically adjust the distance between the surface of gantry 2010 and the surface of docking receptacle 2030. For example, spring(s) 2060 may expand or compress to dynamically adjust the distance between the surface of gantry 2010 and the surface of docking receptacle 2030, and voice coil(s) 2070 may adjust the distance between the surface of gantry 2010 and the surface of docking receptacle 2030 in response to a current passing through the voice coil 2070.

Beneficially, one or more sensor(s) 2080 sense the distance Z" between the surface of gantry 2010 and the surface of docking receptacle 2030, and in response thereto output(s) to controller 4000 one or more sensing signals. In some embodiments, one or more sensor(s) 2080 may sense a change in the distance Z" between the surface of gantry 2010 and the surface of docking receptacle 2030, and in response thereto output(s) to controller 4000 one or more sensing signals.

Controller 4000 may control movement of adjustable table 2020 in response to the sensing signal(s) to maintain a target distance in the Z direction between lens assembly 2040 and a reference area of eye docking assembly 20.

In some embodiments, laser 3000 may be provided as a separate device, apart from the rest of laser surgery system 100. In some embodiments, structural frame 1000 may be provided as a separate element to which the rest of laser surgery system 100 is attached or connected.

Figure 2:
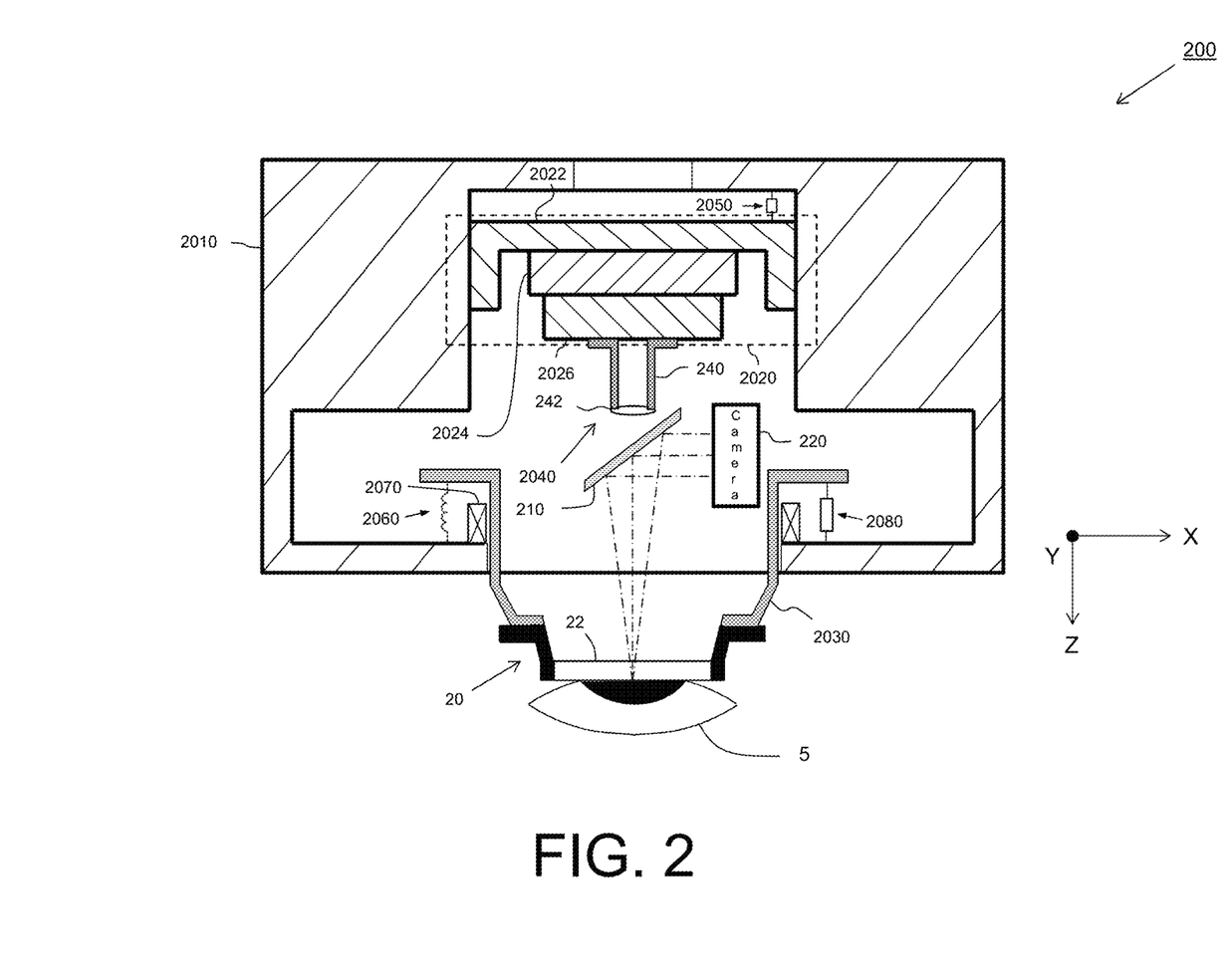
FIG. 2 illustrates an example of a portion of a laser surgery system which employs a camera in an eye docking procedure.

FIG. 2 illustrates an example of a portion of a laser surgery system which employs a camera in an eye docking procedure. Here, laser surgery system 200 is a variation of laser surgery system 100 and so a repeated description of the common elements between laser surgery system 100 and laser surgery system 200 will not be repeated.

Laser surgery system 200 includes a mirror or beamsplitter 210 and an imaging device (e.g., a camera) 220. Here, beamsplitter 210 and an imaging device 220 may be configured to be removably inserted into between lens assembly 2040 and docking receptacle 2030, for example under the control of one or more motors (not shown), after adjustable table 2020 is moved far away from docking receptacle 2030. As will be described in greater detail below, in some embodiments imaging device 220 may produce image data for a patient's eye 5 and provide this image data to a user via a heads-up display and/or to controller 4000, wherein the image data may be used to control movement of gantry 2010 to dock eye docking assembly 20 to docking receptacle 2030 during an eye docking procedure prior to the commencement of laser surgery on the patient's eye 5.

Figure 3:
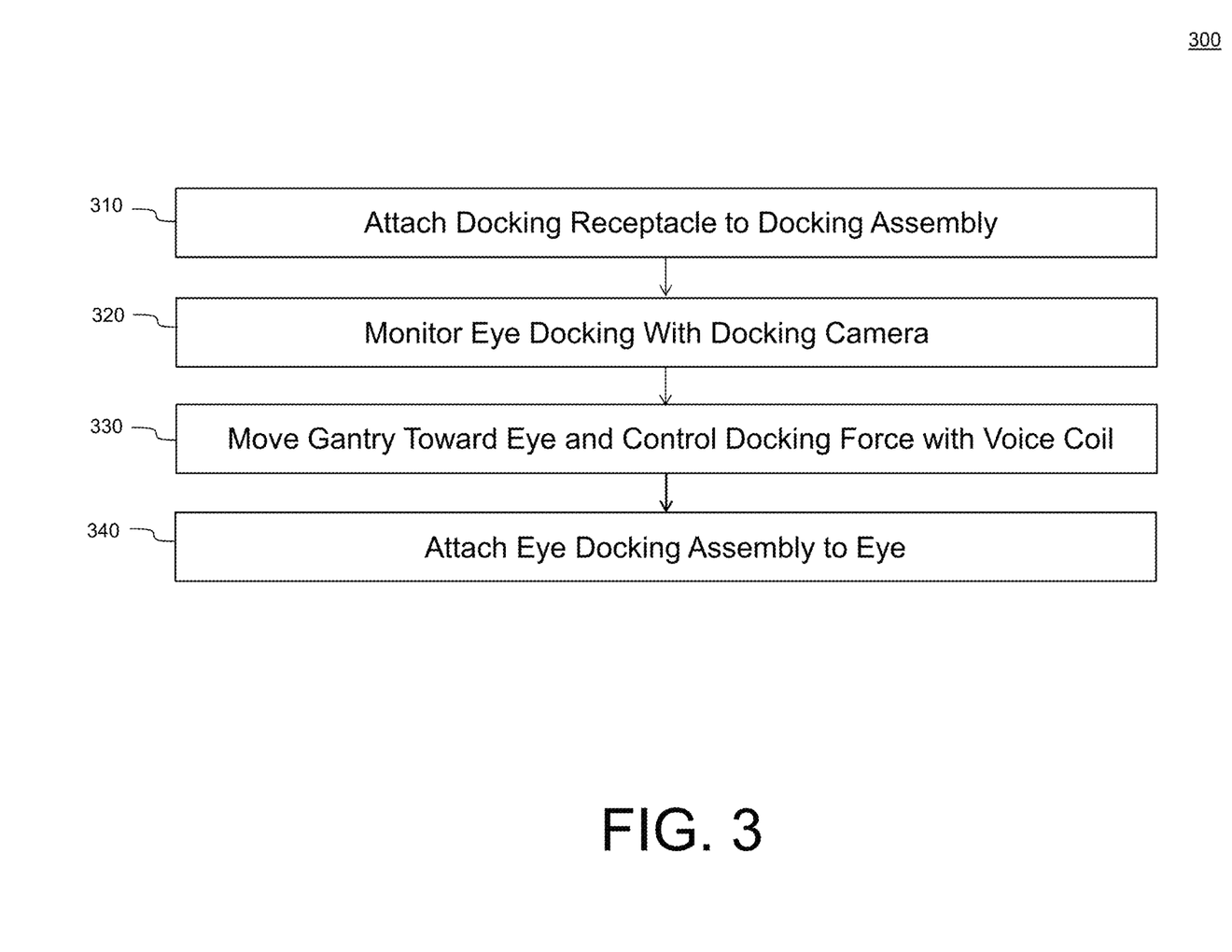
FIG. 3 is a flowchart of a method of docking an eye to a laser surgery system for performing a laser surgery procedure.

FIG. 3 is a flowchart of a method 300 of docking an eye to a laser surgery system (e.g., laser surgery system 100) for performing a laser surgery procedure.

In an operation 310, eye docking assembly 20 is attached with docking receptacle 2030.

In an optional operation 320, the patient's eye 5 may be monitored by imaging device 230 during the docking procedure in embodiments where laser surgery system 100 includes imaging device 220.

At this point, prior to docking, the load on resilient connector(s) (e.g., springs) 2060 and the weight of docking receptacle 2030 produce a balance at an initial distance of distance $Z''=Z''_{INIT}$.

In an operation 330, gantry 2010 is moved toward the patient's eye 5 so as to dock eye docking assembly 20 with the patient's eye 5. During docking, a docking force F is created, where $F=K_S(Z''-Z''_{INIT})-F_V$, where $F_V$ is a motive force generated by connector(s) (e.g., voice coil(s)) 2070 in response to the current which is caused to pass therethrough by controller 4000. Accordingly, it is seen that the docking force may be controlled by the current through the voice coil(s) 2070. Here, sensor(s) 2080 may provide one or more sensing signals to controller 4000 from which controller 4000 may determine Z" and in response to which control the movement of gantry 2010 and the current through voice coil(s) 2070 to provide a smooth docking procedure with minimal loading on the patient and patient's eye 5. At this point, if beamsplitter 210 and imaging device 220 were employed in the docking procedure, then they may be removed from the path between lens assembly 2040 and docking receptacle 2030.

In an operation 340, eye docking assembly 20 is attached to the patient's eye 5 by any of a variety of methods which are known in the art.

Figure 4:
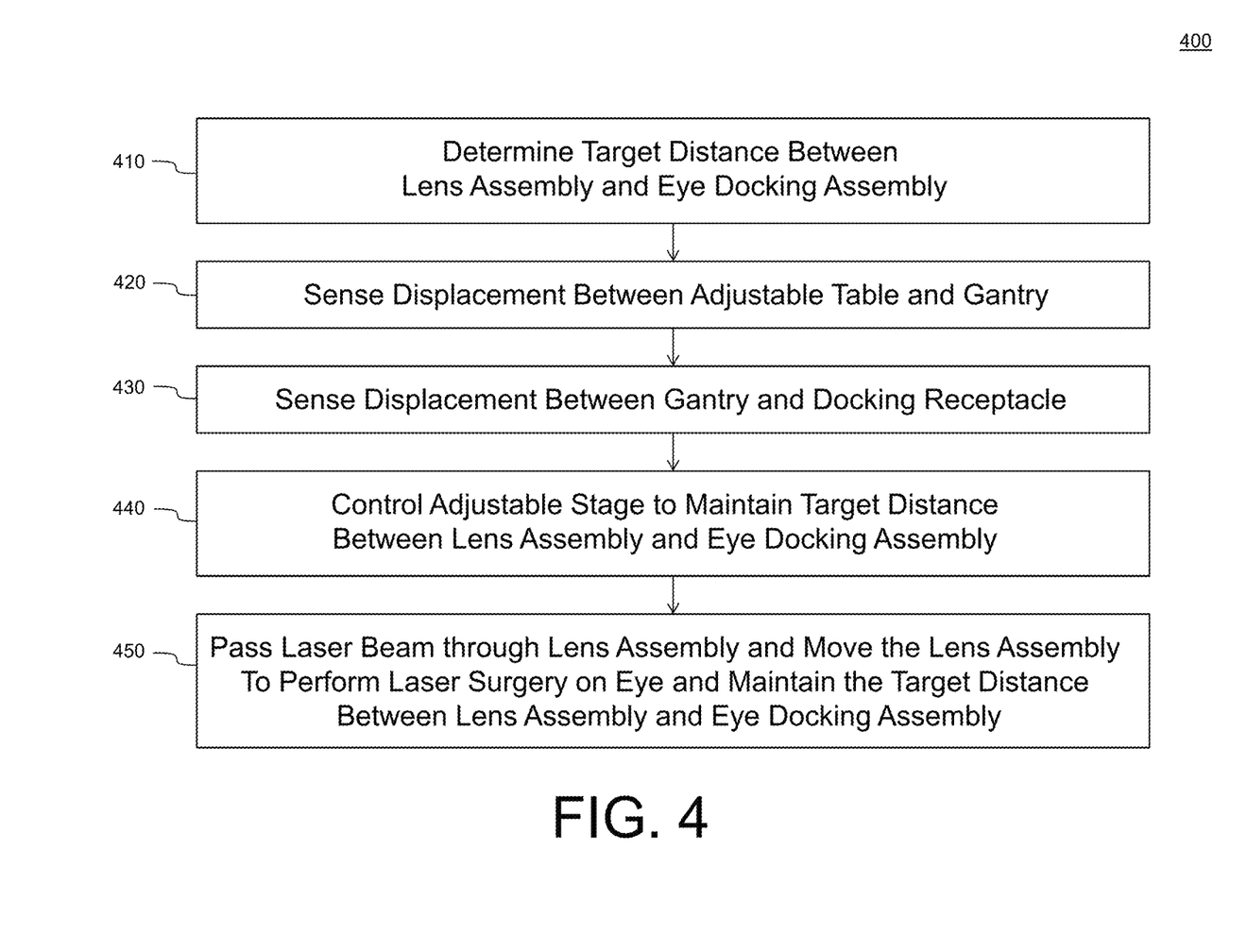
FIG. 4 is a flowchart of a method of performing laser eye surgery.

FIG. 4 is a flowchart of a method 400 of performing laser eye surgery. In some embodiments, method 400 may be performed subsequent to an eye docking procedure such as method 300.

In an operation 410, a laser surgery system, for example a controller of the laser surgery system (e.g., laser surgery system 100) determines a target distance $D_{OPT}$ between lens assembly 240 and eye docking assembly 20, in particular between lens assembly 240 and a reference area of the eye docking assembly, such as the top surface of applanating lens 22.

In an operation 420, one or more sensors (e.g., sensor(s) 2050) sense a displacement Z' between adjustable table 2020 and gantry 2010. Sensor(s) 2050 output one or more sensing signals including a Z stage position sensing signal to controller 4000.

In an operation 430, one or more sensors (e.g., sensor(s) 2080) sense a displacement between gantry 2010 and docking receptacle 2030. In some embodiments, sensor(s) 2080 sense the distance Z" between a surface of gantry 2020 and a surface of docking receptacle 2030 which is attached resiliently to gantry 2010 by the one or more connectors 2060 and/or 270. In some embodiments, sensor(s) 2080 sense a change in the distance Z" between the surface of the gantry and the surface of the docking receptacle. Sensor(s) 2080 may output one or more sensing signals to controller 4000.

In an operation 440, in response to the sensing signal(s) from sensor(s) 2050 and/or sensor(s) 2080, controller 4000 controls adjustable stage 2020 to maintain the target distance $D_{OPT}$ between lens assembly 240 and eye docking assembly 20, in particular between lens assembly 240 and a reference area of the eye docking assembly, such as the top surface of applanating lens 22. In some embodiments, controller 4000 may control a motive force of one or more voice coils 2070 by passing a controlled current therethrough to maintain the target distance $D_{OPT}$ between lens assembly 240 and eye docking assembly 20.

In an operation 450, under control of controller 4000, laser surgery system 100 generates a laser beam and passes the laser beam through lens assembly 2040 and moves lens assembly to direct the laser beam to one or more target areas on the patient's eye 5 to perform a predetermined laser surgery procedure on the patient's eye 5. Throughout operation 450, while the laser is on during the surgery, controller 4000 causes optical assembly 2040 to track movement of patient's eye 5 in the Z direction to maintain the distance $D_{OPT}$ between lens assembly 240 and eye docking assembly 20 regardless of how patient's eye 5 moves in the Z direction during the procedure, thus preventing optical assembly 2040 from touching docking receptacle 2030, eye docking assembly 20, or applanating lens 22.

Through the use of resilient connectors, for example spring(s) 2060 and voice coil(s) 2070 vibration forces of adjustable table 2020 may be added onto gantry 2010 and the heavy structural frame 1000 to which gantry 2010 is attached instead of being loaded onto the patient's eye 5 via docking receptacle 2030. And in the event that electrical power is lost, the resultant docking force is $F=W+K_S(Z''-Z''_{INIT})$, where W is the small weight of eye docking assembly 20 and docking receptacle 2030.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

I claim:

1. A system, comprising:
a structural frame;
a gantry attached to the structural frame and movable relative to the structural frame;
a docking receptacle configured to be removably attached to an eye docking assembly which is attached to an eye;
a plurality of connectors configured to resiliently attach the docking receptacle to the gantry, the plurality of connectors including one or more springs and one or more voice coils which cooperate to generate a docking force between the docking receptacle and the gantry, wherein the docking force includes a first force component generated by the one or more springs and a second force component generated by the one or more voice coils, wherein the first force component is proportional to a difference between a Z-direction distance between a surface of gantry and a surface of docking receptacle and an initial Z-direction distance, the initial Z-direction distance being a distance between the surface of gantry and the surface of docking receptacle at which a load on the one or more springs and a weight of the docking receptacle produce a balance;
an adjustable table attached to the gantry and movable in the Z direction relative to the gantry, the adjustable table including a Z stage configured to move in the Z direction relative to the gantry;
a lens assembly attached to the adjustable table, wherein the adjustable table is configured to move the lens assembly in the Z direction relative to the eye;
at least one sensor configured to sense at least one of (1) the distance between the surface of the gantry and the surface of the docking receptacle which is attached resiliently to the gantry by the one or more connectors, and (2) a change in the distance between the surface of the gantry and the surface of the docking receptacle, and in response thereto to output at least one sensing signal; and
a controller configured to control movement of the adjustable table in response to the at least one sensing signal to maintain a target distance between the lens assembly and a reference area of the eye docking assembly,
wherein the controller is further configured to control, in response to the at least one sensing signal, an amount of current which passes through at least one of the one or more voice coils to minimize the docking force between the docking receptacle and the gantry.

2. The system of claim 1, further including a laser source.

3. The system of claim 1, further comprising a Z stage sensor configured to sense a displacement of the Z stage with respect to the gantry and in response thereto to output a Z stage position sensing signal, wherein the controller is configured to control movement of the Z stage in response to the Z stage position sensing signal to maintain the target distance between the lens assembly and the reference area of the eye docking assembly.

4. The system of claim 1, further comprising an imaging device configured to produce image data for the eye, wherein the controller is configured to use the image data to control movement of the gantry relative to the eye.

5. A method, comprising:
resiliently attaching a docking receptacle to a gantry by one or more springs and one or more voice coils, wherein the one or more springs and one or more voice coils cooperate to generate a docking force between the docking receptacle and the gantry, wherein the docking force includes a first force component generated by the one or more springs and a second force component generated by the one or more voice coils, wherein the first force component is proportional to a difference between a Z-direction distance between a surface of gantry and a surface of docking receptacle and an initial Z-direction distance, the initial Z-direction distance being a distance between the surface of gantry and the surface of docking receptacle at which a load on the one or more springs and a weight of the docking receptacle produce a balance;
removably attaching the docking receptacle to an eye docking assembly which is attached to an eye;
sensing at least one of (1) the distance between the surface of the gantry and the surface of the docking receptacle, and (2) a change in the distance between the surface of the gantry and the surface of the docking receptacle, and in response thereto outputting at least one sensing signal;
passing a laser beam from a laser source through a lens assembly which is attached to an adjustable table which is attached to the gantry and which adjustable table is configured to move the lens assembly in a Z direction with respect to the eye, the adjustable table including a Z stage configured to move the lens assembly in a Z direction;

the adjustable table moving the lens assembly in the Z direction relative to the eye so as to direct the laser beam to one or more target areas of the eye to perform a laser surgery on the eye;

controlling movement of the adjustable table in response to the at least one sensing signal to maintain focus of the laser beam at a desired depth of the eye; and controlling an amount of current which passes through at least one of the one or more voice coils in response to the at least one sensing signal to minimize the docking force between the docking receptacle and the gantry.

6. The method of claim 5, wherein the controlling movement of the adjustable table in response to the at least one sensing signal includes controlling movement of the Z stage to maintain a desired distance between the lens assembly and a reference area of the eye docking assembly.

7. A system, comprising:

a gantry configured to be attached to a structural frame;

a docking receptacle configured to be removably attached to an eye docking assembly which is attached to an eye;

an adjustable table attached to the gantry, the adjustable table including at least a Z stage configured to move in a Z direction relative to the gantry;

a lens assembly attached to the adjustable table, wherein the adjustable table is configured to move the lens assembly relative to the gantry;

a plurality of connectors configured to attach the docking receptacle to the gantry, the plurality of connectors including one or more springs and one or more voice coils which cooperate to generate a docking force between the docking receptacle and the gantry, wherein the docking force includes a first force component generated by the one or more springs and a second force component generated by the one or more voice coils, wherein the first force component is proportional to a difference between a Z-direction distance between a surface of gantry and a surface of docking receptacle and an initial Z-direction distance, the initial Z-direction distance being a distance between the surface of gantry and the surface of docking receptacle at which a load on the one or more springs and a weight of the docking receptacle produce a balance;

at least one sensor configured to sense at least one of (1) the distance between the surface of the gantry and the surface of the docking receptacle, and (2) a change in the distance between the surface of the gantry and the surface of the docking receptacle, and in response thereto outputting at least one sensing signal; and a controller configured to maintain, in response to the at least one sensing signal, a target distance between the lens assembly and a reference area of the eye docking assembly, wherein the controller is further configured to control, in response to the at least one sensing signal, an amount of current which passes through at least one of the one or more voice coils to minimize the docking force between the docking receptacle and the gantry.

8. The system of claim 7, wherein the controller is configured to maintain the target distance between the lens assembly and a reference area of the eye docking assembly by at least one of (1) controlling movement of the adjustable table in a direction from the lens assembly to the eye docking assembly, and (2) controlling an amount of current passing through the one or more voice coils.

9. The system of claim 7, wherein the controller is configured to maintain the target distance between the lens assembly and the reference area of the eye docking assembly in response to the at least one sensing signal by controlling a movement of the adjustable table in a direction from the lens assembly to the eye docking assembly.

* * * * *